(12) United States Patent
Horne et al.

(10) Patent No.: US 6,841,685 B2
(45) Date of Patent: Jan. 11, 2005

(54) METHODS FOR MAKING BIS-HETEROCYCLIC ALKALOIDS

(75) Inventors: David A. Horne, Corvallis, OR (US); Kenichi Yakushijin, Corvallis, OR (US)

(73) Assignee: State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 0 days.

(21) Appl. No.: 10/297,688

(22) PCT Filed: Jun. 7, 2001

(86) PCT No.: PCT/US01/18584

§ 371 (c)(1),
(2), (4) Date: Dec. 5, 2002

(87) PCT Pub. No.: WO01/94310

PCT Pub. Date: Dec. 13, 2001

(65) Prior Publication Data

US 2003/0232988 A1 Dec. 18, 2003

Related U.S. Application Data

(60) Provisional application No. 60/210,145, filed on Jun. 7, 2000, and provisional application No. 60/221,277, filed on Jul. 27, 2000.

(51) Int. Cl.[7] .................. C07D 209/12; C07D 209/18; A61K 31/405
(52) U.S. Cl. ..................... 548/493; 548/490; 548/493; 514/415; 514/419
(58) Field of Search ............................ 548/490, 493; 514/415, 419

(56) References Cited

U.S. PATENT DOCUMENTS

5,936,098 A    8/1999   Yasuda et al.

OTHER PUBLICATIONS

CAPLUS abstract of Hogan, I. T. and Sainsbury, M. The Synthesis of dendrodoine, 5–[3–(N,N–dimethylamino–1,2, 4–thiadiazolyl]–3–indolylmethanone, a metabolite of the marine tunicate Dendroda grossular. Tetrahedron (1984). vol. 40 (4), pp 681–2.*

CAPLUS abstact of Ogura, Fumio et al. JP 63079848, Manufacture of carbonyl compounds by oxidation of hydroxyl compounds in the presence of aryl tellurinic acid anhydrides. Apr. 9, 1998.*

* cited by examiner

Primary Examiner—Ceila Chang
Assistant Examiner—Janet L Coppins
(74) Attorney, Agent, or Firm—Klarquist Sparkman, LLP

(57) ABSTRACT

Methods for making bis-heterocyclic compounds, especially bis-heterocyclic compounds having five and six-membered heterocyclic linkers are described. Also described are methods for making an alpha amino ketone synthon that enables facile syntheses of bisindole compounds, including topsentins and dragmacidins

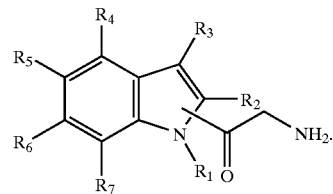

6 Claims, No Drawings

METHODS FOR MAKING BIS-HETEROCYCLIC ALKALOIDS

CROSS REFERENCE TO RELATED APPLICATIONS

The present application claims the benefit of the earlier filing dates of U.S. provisional patent application No. 60/210,145, filed Jun. 7, 2000 and U.S. provisional patent application No. 60/221,277 filed Jul. 27, 2000 both of which are incorporated herein by reference.

ACKNOWLEDGEMENT OF GOVERNMENTAL SUPPORT

The present invention was developed, at least in part, using governmental funds provided by the National Institutes of Health under contract number GM 50929. The United States government may have certain rights to this invention.

FIELD

The present invention concerns bis-heterocyclic alkaloids, including bisindole compounds, and methods for their synthesis.

BACKGROUND

Marine sponges produce a number of bioactive, bisindole metabolites containing either an imidazole- or a piperazine-derived linker unit. These compounds have received much attention due to their potent biological activities as antitumor, antiviral, and antiinflammatory agents. The bisindole alkaloid topsentin A 1 is representative of a class of deep-sea sponge bisindole metabolites that contain an imidazole linker. The nortopsentins, including nortopsentin B 2 and nortopsentin D 3, also are examples of bisindole sponge metabolites with an imidazole linker. The 2,5-bis(3'-indolyl) piperazine alkaloids, dragmacidin B 4 (from the sponge, *Hexadella* sp.) and 2,5-bis (6'-bromo-3'-indolyl)piperazine 5 (from the tunicate, *Didemnum candidum*) are representative of a group of bisindole metabolites containing a piperazine linker. Biosynthetically, dragmacidins and topsentins are conceivably derived by the condensation of two tryptamine derivatives in either a head-to-head (topsentins) or head-to-tail (dragmacidins) orientation.

Compound 1

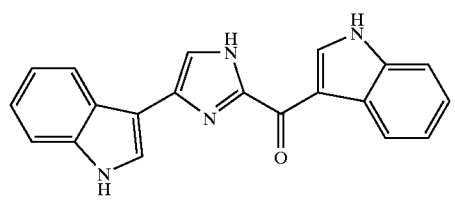

Compound 2

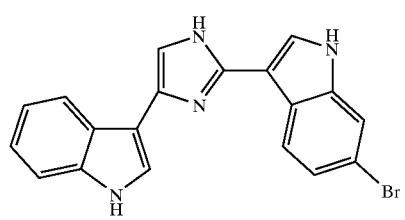

Compound 3

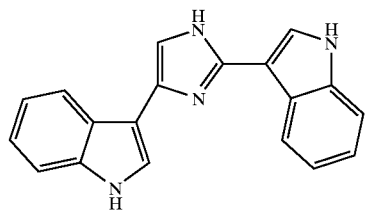

Compound 4

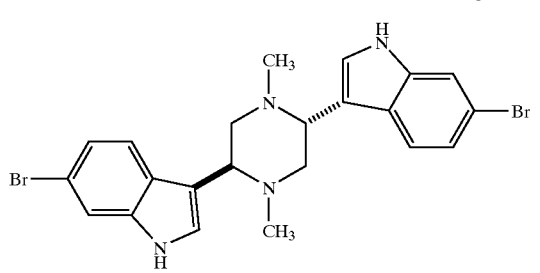

Compound 5

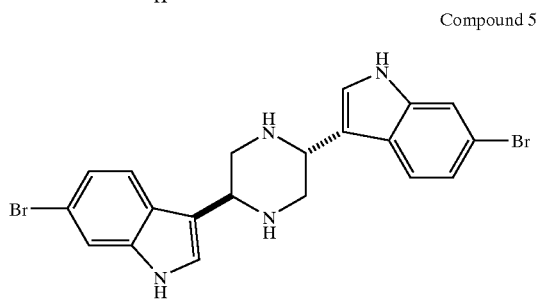

Previous syntheses of bis(indolyl)imidazoles have been accomplished via palladium-catalyzed cross coupling of 3-indolylboronic acids or 3-stannylindoles with halogenoimidazoles (See, for example, Kawasaki et al., *J. Chem. Soc., Chem. Commun.*, 1994, 2085), rearrangement and dimerization of hydrazinium bromide prepared from 3-bromoacetylindole (See, for example, Braekman et al., *Pure & Appl. Chem.*, 1989, 61, 509), and oxidative dimerization of 3-hydroxyacetylindoles using Cu(OAc)$_2$ and NH$_4$OH (See, for example, Tsugi, et al., *J. Org. Chem.*, 1998, 53, 5446).

Despite the broad range of biological activity exhibited by the class of bis(indolyl)piperazines, including cytotoxicity, only two reports have described the successful construction of the piperazine ring system (See, Witlock and Cava *Tetrahedron Lett.*, 1994, 35, 371 and Jiang et al, *J. Org. Chem.*, 1994, 59, 6823). In both reports, access to the substituted piperazines was achieved via diborane reduction of diketopiperazine intermediates.

SUMMARY

The present invention provides methods for making compounds that have a structure according to the general formula:

$$A_1—M—A_2$$

wherein A$_1$ and A$_2$ are heterocycles and M is a linker moiety that joins the two heterocycles, A$_1$ and A$_2$, into a bis-heterocyclic compound. The heterocycles, A$_1$ and A$_2$, can be the same or different. The heterocycles A$_1$ and A$_2$ can be, for example and without limitation, indole, pyridine, pyrimidine, purine, pyrrole, furan, thiophene, imidazole, benzimidazole, oxazole, thiazole, pyrazole, 3-pyrroline, pyrrolidine, quinolone, isoquinolone, carbazole, cyclic anhydride, cyclic imide, cyclic lactone, and the like. The heterocycles can be aromatic or non-aromatic. If the heterocycles $A_1$ and $A_2$ comprise indole, the compound is a bisindole compound. The heterocycles can be joined to the linker moiety at any position on the heterocyclic ring. When the linker moiety comprises a ring structure, the heterocycles $A_1$ and $A_2$ can be joined thereto at any position on the linker moiety.

In particular embodiments, methods are provided for making bisindole compounds of the general formula:

Indole-M-Indole wherein linker moiety M, for disclosed embodiments, typically comprises a ring structure selected from the group consisting of pyrazine, piperazine, imidazole, and oxazole. The indole rings may be joined to the linker moiety at any position on the indole rings and any position on the ring of the linker moiety. In other particular embodiments the linker moiety comprises an amide and the indole rings may be joined to the linker moiety at any position on the indole rings.

In some embodiments, methods are provided for making bisindole compounds of Formula 1.

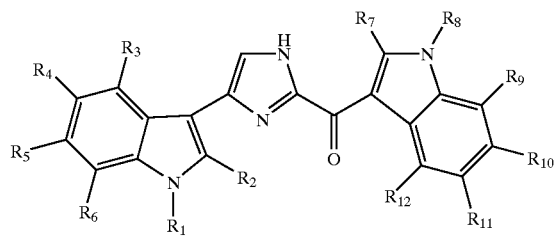

Formula 1

Compounds with Formula 1 are referred to herein as topsentins.

In other embodiments, methods for making compounds of Formula 2 are disclosed.

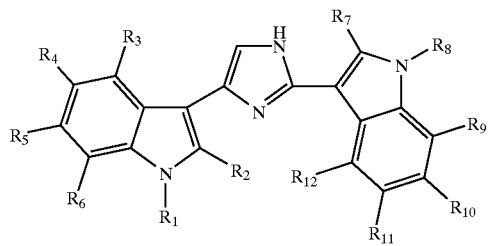

Formula 2

Compounds with Formula 2 are referred to herein as nortopsentins.

In some embodiments, methods for making bisindole compounds of Formula 3 are disclosed.

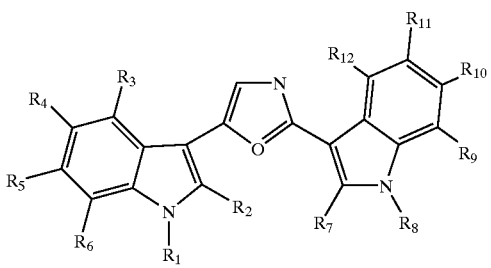

Formula 3

In other embodiments, methods for making bisindole compounds of Formula 4 are disclosed.

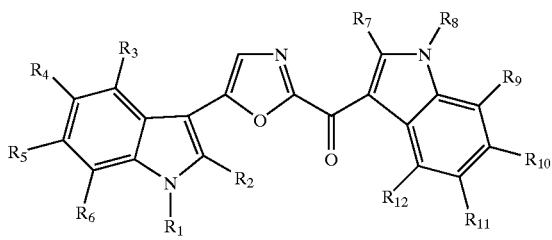

Formula 4

In some embodiments, methods for making bisindole compounds of Formula 5 are disclosed.

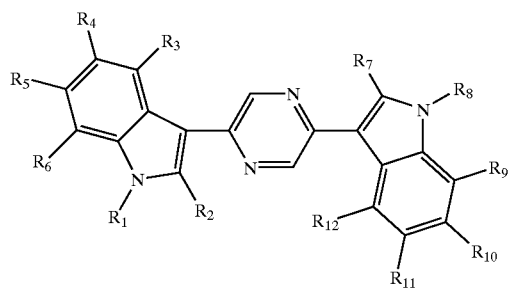

Formula 5

In other embodiments, methods for making bisindole compounds of Formula 6 are disclosed.

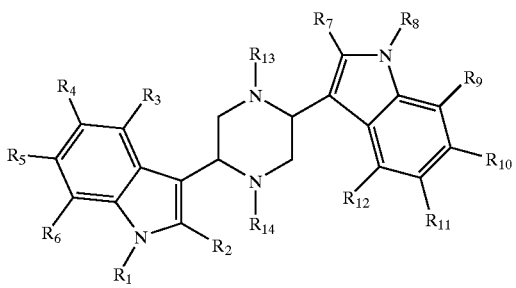

Formula 6

Compounds with Formula 6 are referred to herein as dragmacidins.

In some embodiments, methods for making bisindole compounds of Formula 7 are disclosed.

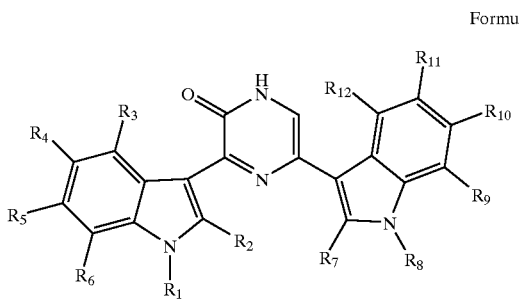

In other embodiments, methods for making bisindole compounds of Formula 8 are disclosed.

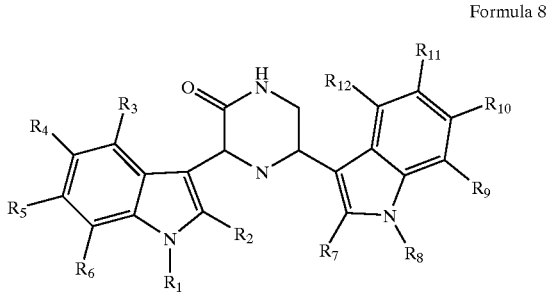

In other embodiments, methods for making bisindole compounds of Formula 9 are disclosed.

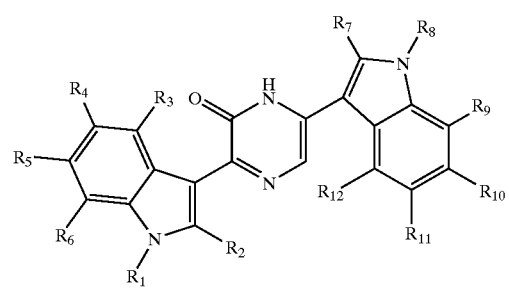

In other embodiments, methods for making bisindole compounds of Formula 10 are disclosed.

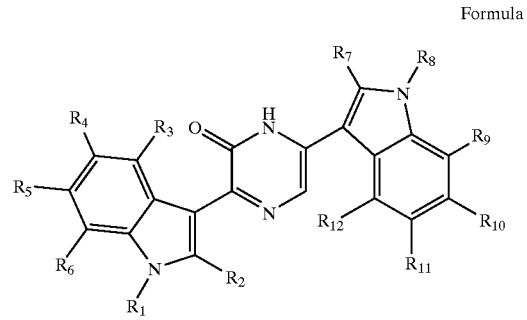

In some embodiments, methods for making bisindole compounds of Formula 11 are disclosed.

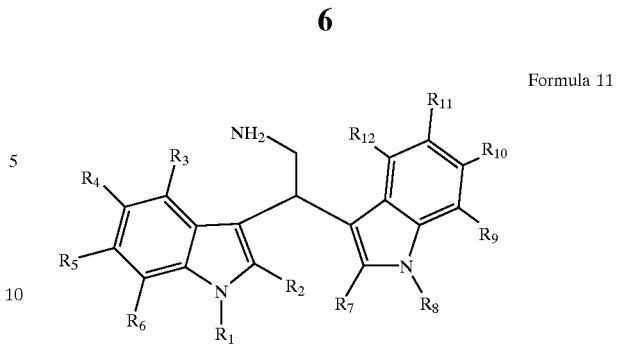

With reference to Formulas 1 through 11, the groups $R_1$ through $R_{12}$ are independently selected from the group consisting of hydrogen, hydroxy, halogen, lower aliphatic, particularly lower alkyl, lower alkoxy, and lower acyl. The term "lower" refers to organic radicals having 10 or fewer carbon atoms, including all straight and branched-chain isomers and stereoisomers. The term "aliphatic" refers to alkyl, alkenyl, and alkynyl radicals, including substituted derivatives thereof.

In another aspect, methods for making alpha amino ketones of Formula 12 are disclosed. Such alpha amino ketone synthons are particularly useful for synthesizing a wide variety of compounds, including compounds of Formulas 1 through 12. The methods for making these synthons disclosed herein provide synthetic advantages relative to other known methods.

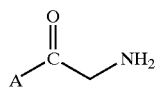

With respect to Formula 12, A is a heterocycle comprising a ring system selected from the group of indole, pyridine, pyrimidine, purine, pyrrole, furan, thiophene, imidazole, benzimidazole, oxazole, thiazole, pyrazole, 3-pyrroline, pyrrolidine, quinolone, isoquinolone, carbazole, cyclic anhydride, cyclic imide, cyclic lactone, and the like. The alpha amino ketone portion may be joined to heterocycle A at any position on the heterocycle. In a particular embodiment, A is indole and the alpha amino ketone is attached at any position around the indole ring, such as shown in Formula 13.

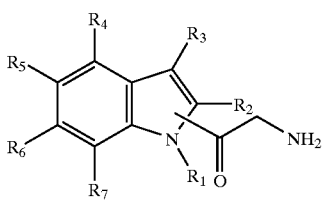

With reference to Formula 13, the alpha amino ketone group may replace any of the groups labeled $R_1$ through $R_7$. The remaining R groups may be independently selected from the group consisting of hydrogen, hydroxy, halogen, lower aliphatic, particularly lower alkyl, lower alkoxy, and lower acyl.

In some embodiments, methods of making alpha amino ketones of Formula 11 are provided.

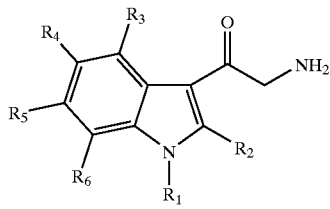

Formula 11

With reference to Formula 11, the groups $R_1$ through $R_6$ are independently selected from the group consisting of hydrogen, hydroxy, halogen, lower aliphatic, particularly lower alkyl, lower alkoxy, and lower acyl.

DETAILED DESCRIPTION

The present invention includes a method for converting an acyl cyanide to an alpha amino ketone. In general, the method comprises providing an acyl cyanide, and converting the acyl cyanide to an alpha amino ketone, such as by catalytic hydrogenation. In some embodiments the acyl cyanide has the formula

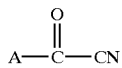

where A comprises a heterocyle selected from the group consisting of indole, pyridine, pyrimidine, purine, pyrrole, furan, thiophene, imidazole, benzimidazole, oxazole, thiazole, pyrazole, 3-pyrroline, pyrrolidine, quinolone, isoquinolone, carbazole, cyclic anhydride, cyclic imide, and cyclic lactone. The acyl cyanide group may be attached to heterocycle A in any position around the heterocycle.

In some embodiments, the acyl cyanide has the formula

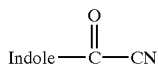

where indole comprises an indole ring and, in particular embodiments, the acyl cyanide has the formula

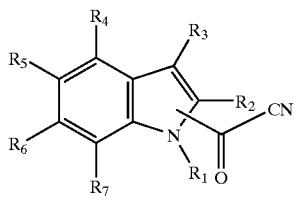

where the acyl cyano group may replace any of the groups labeled $R_1$ through $R_7$. The remaining R groups may be independently selected from the group consisting of hydrogen, hydroxy, halogen, lower aliphatic, particularly lower alkyl, lower alkoxy, and lower acyl.

In more particular embodiments, the acyl cyanide has the formula

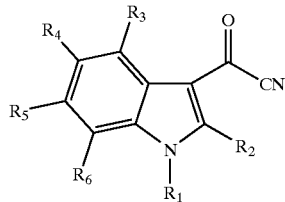

where $R_1$, $R_2$, $R_3$, $R_4$, $R_5$, and $R_6$ are independently selected from the group consisting of hydrogen, hydroxy, halogen, lower aliphatic, lower alkoxy, and lower acyl.

The acyl cyanide may be converted to the alpha amino ketone by exposing the acyl cyanide to hydrogen in the presence of a hydrogenation catalyst. In a particular embodiment, the hydrogenation catalyst is palladium carbon.

The present invention also includes a method for making an imidazole compound of formula

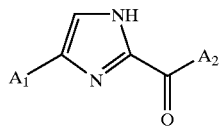

including topsentins. The disclosed embodiments comprised providing a first alpha amino ketone compound of formula

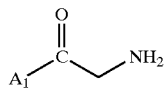

and providing a second alpha amino ketone compound of formula

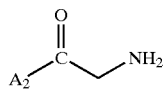

A mixture was formed comprising the first and second alpha amino ketone compounds, and the mixture was contacted with air to form the imidazole compound. $A_1$ and $A_2$ may be the same or different. In particular embodiments, $A_1$ and $A_2$ comprise an indole ring, and in more particular embodiments the first and second alpha amino ketone compounds have the formula

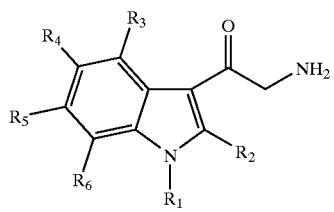

where $R_1$, $R_2$, $R_3$, $R_4$, $R_5$, and $R_6$ are independently selected from the group consisting of hydrogen, hydroxy, halogen, lower aliphatic, lower alkoxy, and lower acyl.

The present invention also provides a method for making an imidazole compound of formula

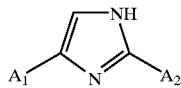

including nortopsentins Disclosed embodiments of the method comprise providing a cyano compound of formula

and providing an alpha amino ketone compound of formula

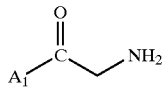

A mixture of the first and second compounds is formed, and heated to form the imidazole compound. Again $A_1$ and $A_2$ may be the same or different. In particular embodiments, $A_1$ and $A_2$ comprise an indole ring. In more particular embodiments, the cyano compound has the formula

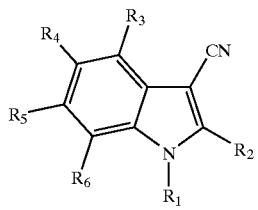

where $R_1, R_2, R_3, R_4, R_5$, and $R_6$ are independently selected from the group consisting of hydrogen, hydroxy, halogen, lower aliphatic, lower alkoxy, and lower acyl, and the alpha amino ketone compound has the formula

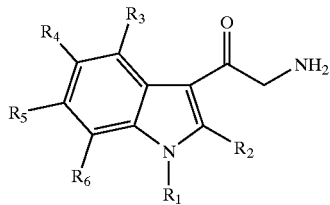

where $R_1, R_2, R_3, R_4, R_5$, and $R_6$ are independently selected from the group consisting of hydrogen, hydroxy, halogen, lower aliphatic, lower alkoxy, and lower acyl.

The present invention also provides a method for making a pyrazine compound of formula

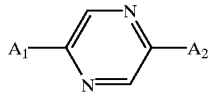

Disclosed embodiments comprised providing an alpha amino ketone compound of formula

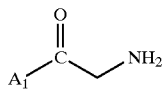

and providing a second alpha amino ketone compound of formula

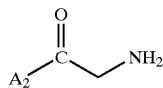

A mixture was formed comprising the first and second compounds. The mixture was heated while excluding air to form the pyrazine compound. $A_1$ and $A_2$ may be the same or different. In particular embodiments $A_1$ and $A_2$ comprise an indole ring, and in more particular embodiments, the two compounds have the formula

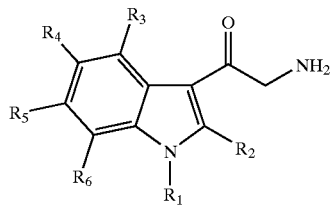

where $R_1, R_2, R_3, R_4, R_5$, and $R_6$ are independently selected from the group consisting of hydrogen, hydroxy, halogen, lower aliphatic, lower alkoxy, and lower acyl.

Methods of reducing a pyrazine compound of formula

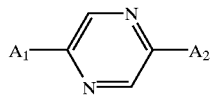

to form a piperazine compound of formula

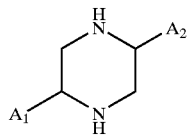

are also disclosed. In a particular disclosed embodiment, the pyrazine compound is reduced by exposing the pyrazine compound to $NaBH_3CN$ in acetic acid solution. In a more particular disclosed embodiment, the piperazine compound formed by this method is Dragmacidin B.

According to the disclosure, pyrazine compounds of formula

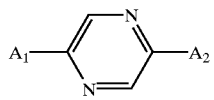

also may be reductively alkylated, such as methylated, to form piperazine compounds of formula

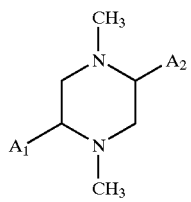

In a particular disclosed embodiment, reductive alkylation was performed by exposing the pyrazine compound to NaBH₃CN in formic acid solution. In a more particular disclosed embodiment, 2,5-bis(6'-bromo-3'-indolyl) piperazine was synthesized by this method.

The present invention also provides methods for making amide compounds of formula

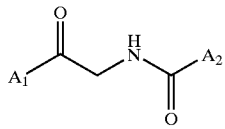

Disclosed embodiments of the method comprise providing an alpha amino ketone compound of formula

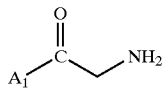

and providing an acyl cyanide compound of formula

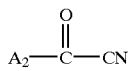

A mixture of the first and second compounds is formed to make the amide compound. Again, $A_1$ and $A_2$ may be the same or different. In some embodiments, $A_1$ and $A_2$ comprise an indole ring. In more particular embodiments the alpha amino ketone compound has the formula

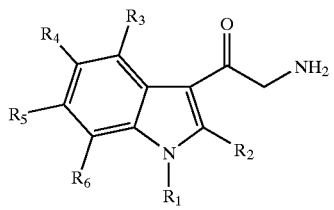

and the acyl cyanide compound has the formula

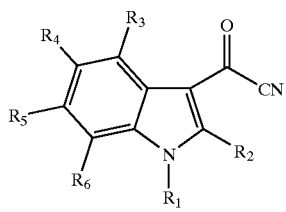

For both compounds, $R_1$, $R_2$, $R_3$, $R_4$, $R_5$, and $R_6$ are independently selected from the group consisting of hydrogen, hydroxy, halogen, lower aliphatic, lower alkoxy, and lower acyl.

According to the disclosure, amide compounds of formula

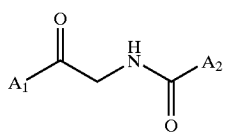

may be cyclodehydrated to make an oxazole compounds of formula

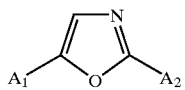

The present invention also provides methods for making amide compounds of formula

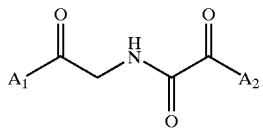

Disclosed embodiments of the method comprise forming a mixture of an alpha amino ketone compound of formula

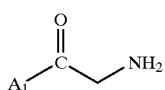

and a second compound of formula

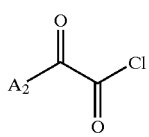

to make the amide compound. $A_1$ and $A_2$ may be the same or different. In one embodiment $A_1$ and $A_2$ comprise an indole ring. In more particular embodiments, the alpha amino ketone compound has the formula

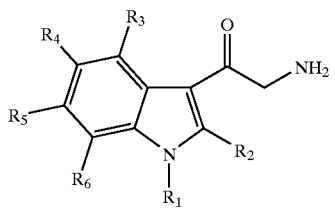

and the acyl cyanide compound has the formula

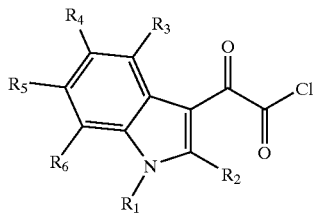

For both compounds, $R_1$, $R_2$, $R_3$, $R_4$, $R_5$, and $R_6$ are independently selected from the group consisting of hydrogen, hydroxy, halogen, lower aliphatic, lower alkoxy, and lower acyl.

The present invention also provides a method for making a compound of formula

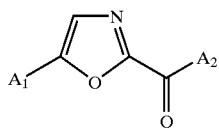

Disclosed embodiments of the method comprise heating an amide compound of formula

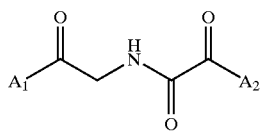

in ammonium hydroxide to form a first compound of formula

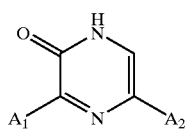

This compound can be reduced to form a compound of formula

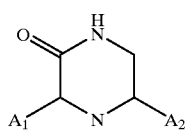

or reductively alkylated to form a compound of formula

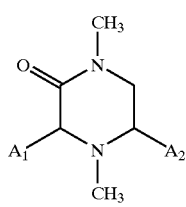

In particular embodiments, reduction was accomplished using NaBH$_3$CN in acetic acid solution and reductive methylation was accomplished using NaBH$_3$CN in formic acid solution.

The present invention further provides methods for making compounds of formulas

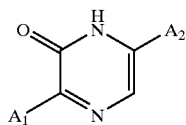

Disclosed embodiments of the method comprise making a mixture of a compound of formula

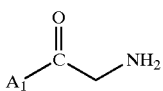

and a compound of formula

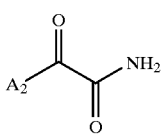

In one aspect, the methods disclosed herein provide short syntheses of bioactive topsentin A and nortopsentins B 2 and D 3 from readily available starting materials. The methods also provide oxazole and pyrazine analogs of these bioactive compounds. The syntheses are highly symmetrical in nature, and represent an efficient entry to this bioactive class of bisindole compounds. Syntheses according to the disclosed methods may find further application to other latent α-amino ketone derived natural products.

Persons of ordinary skill in the art will recognize that the following Schemes illustrate representative examples of general methods for making bisheterocyclic compounds and the intermediates used in those methods. Persons of ordinary skill in the art will further recognize that the indole rings in the following Schemes may have different substituents and substitution patterns from those illustrated. For example, the bromine atoms that appear in some of the compounds of these Schemes may appear at any position on the indole rings or may be replaced with other halogens.

In a disclosed embodiment, oxotryptamine 8 is prepared according to Scheme 1 below.

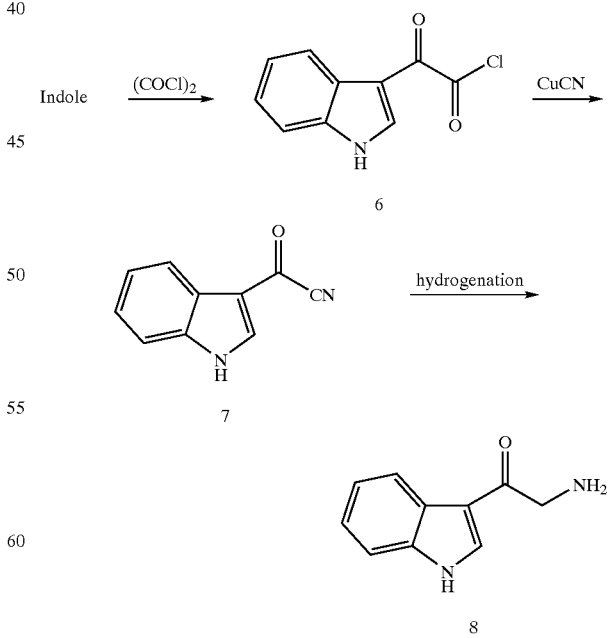

Oxotryptamine synthons such as 8 may be utilized in a wide variety of methods as disclosed. In one disclosed embodiment the synthon is used to produce analogs of topsentins and nortopsentins with oxazole linkers. In a particular disclosed embodiment, unsubstituted oxazole analogs of topsentin and nortopsentin were synthesized according to Scheme 2 below.

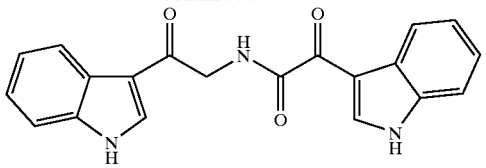

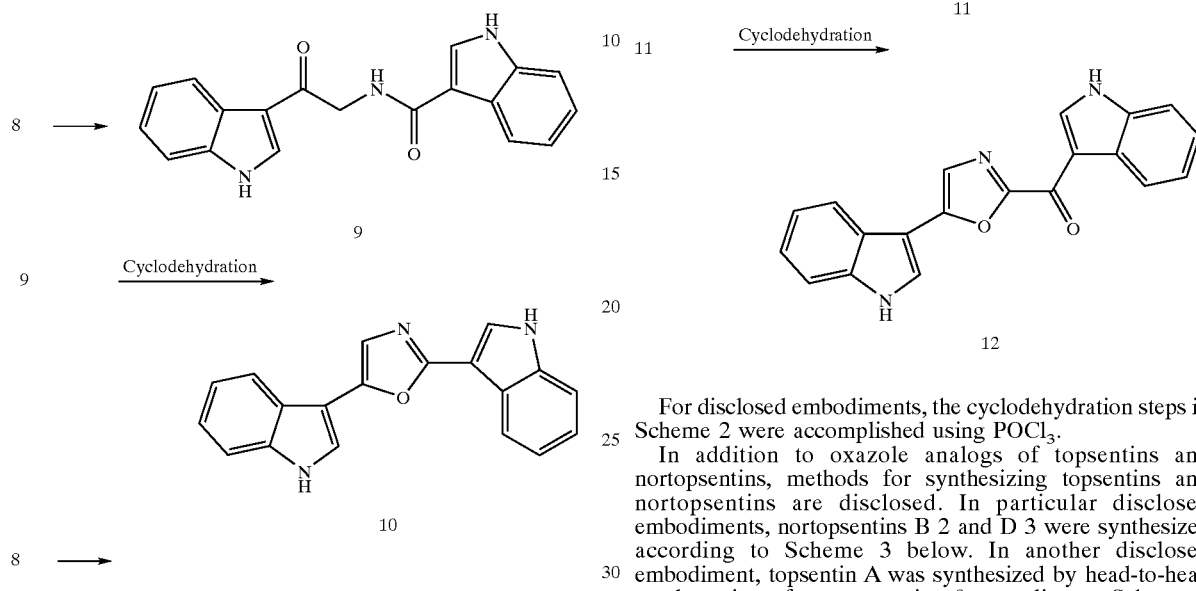

For disclosed embodiments, the cyclodehydration steps in Scheme 2 were accomplished using POCl₃.

In addition to oxazole analogs of topsentins and nortopsentins, methods for synthesizing topsentins and nortopsentins are disclosed. In particular disclosed embodiments, nortopsentins B 2 and D 3 were synthesized according to Scheme 3 below. In another disclosed embodiment, topsentin A was synthesized by head-to-head condensation of oxotryptamine 8 according to Scheme 4 below.

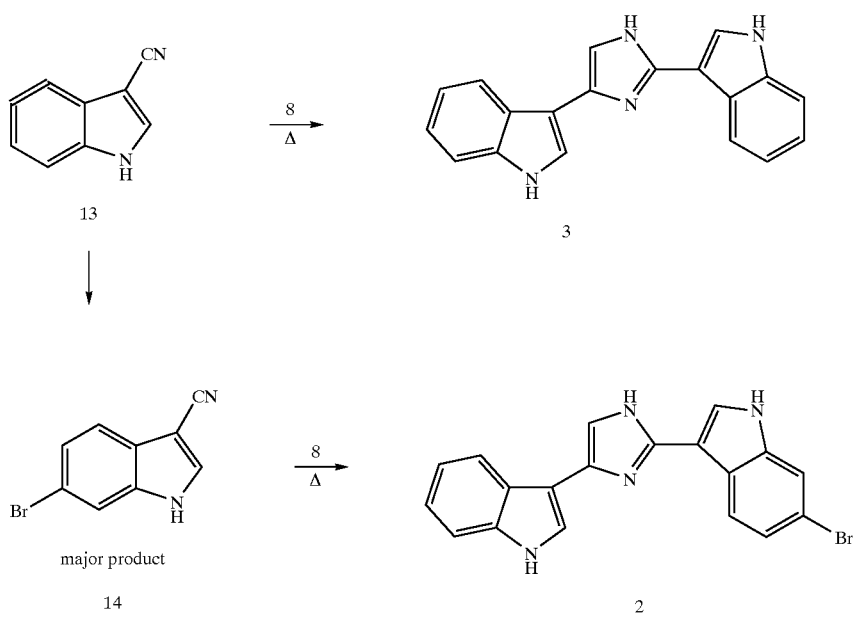

-continued

Scheme 4

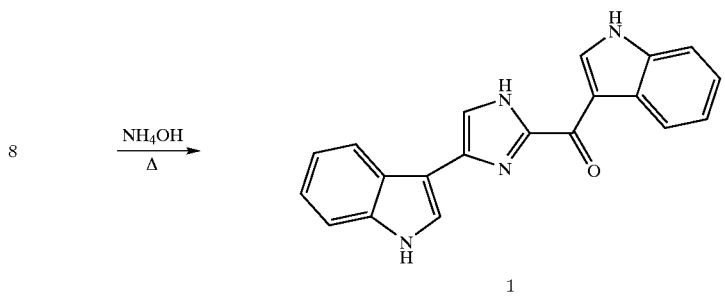

Pyrazine-linked bisindole compounds also may be synthesized using the disclosed oxotryptamine synthon approach. In one embodiment, an unsubstituted pyrazine-linked bisindole compound may be synthesized according to Scheme 5 below.

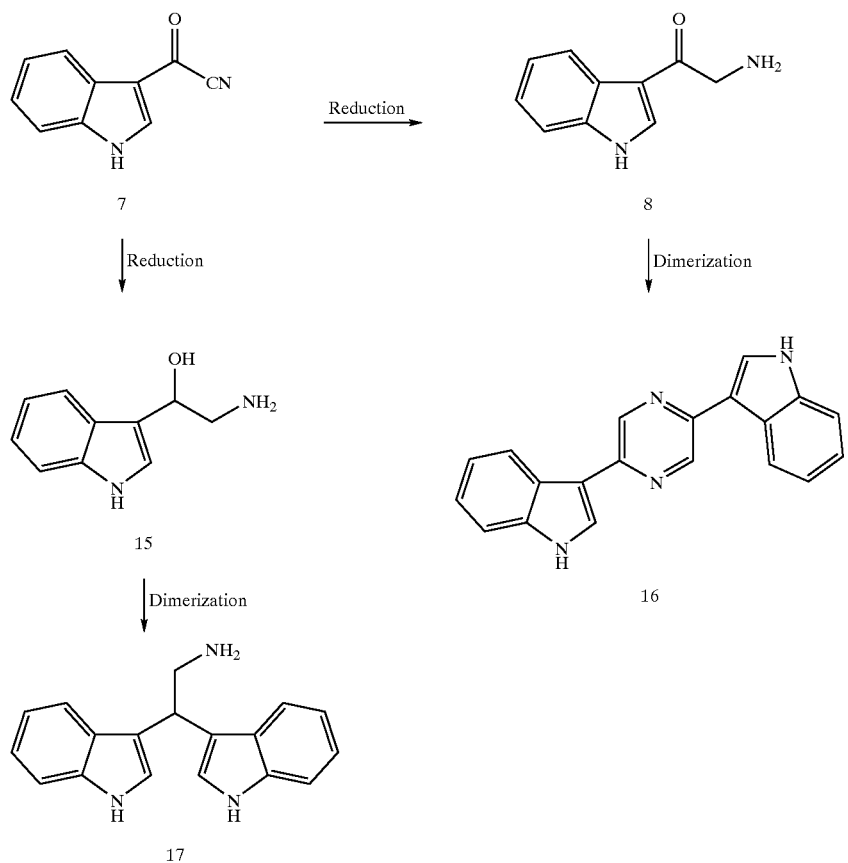

Piperazine-linked bisindole compounds also may be synthesized by selective reduction of pyrazine-linked bisindole compounds. For example, the synthesis of unsubstituted piperazine-linked and dimethyl piperazine-linked bisindole compounds may be accomplished according to Scheme 6 below.

Scheme 6

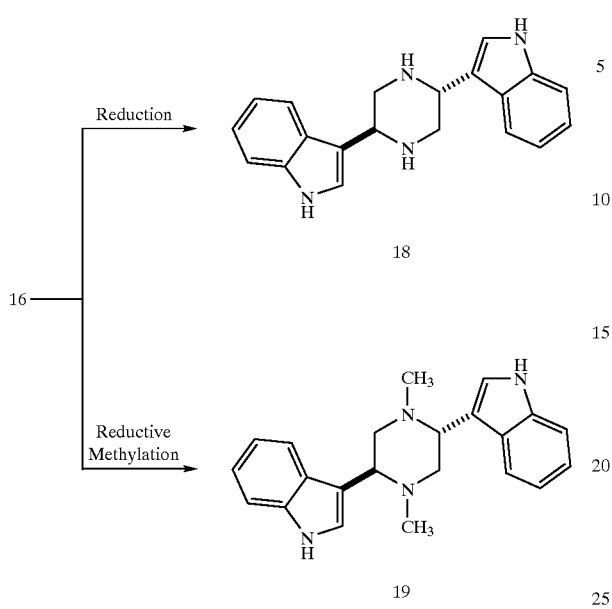

Dragmacidins and dragmacidin analogs may be synthesized from substituted oxotryptamine synthons through reduction or reductive alkylation of pyrazine-linked bisindole intermediates. For example, Scheme 7 outlines the synthesis of Dramacidin B 4 and 2,5-bis(6'-bromo-3'-indoyl) piperazine 5.

Scheme 8 illustrates the synthesis of a pyrimidinone-linked bisindole compound and its reduction.

Scheme 8

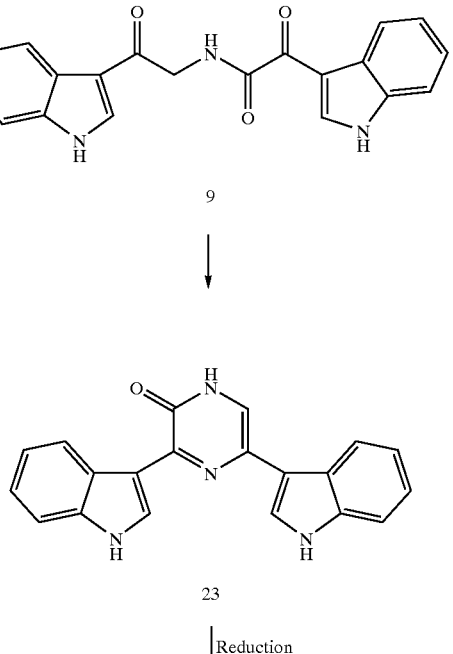

Scheme 7

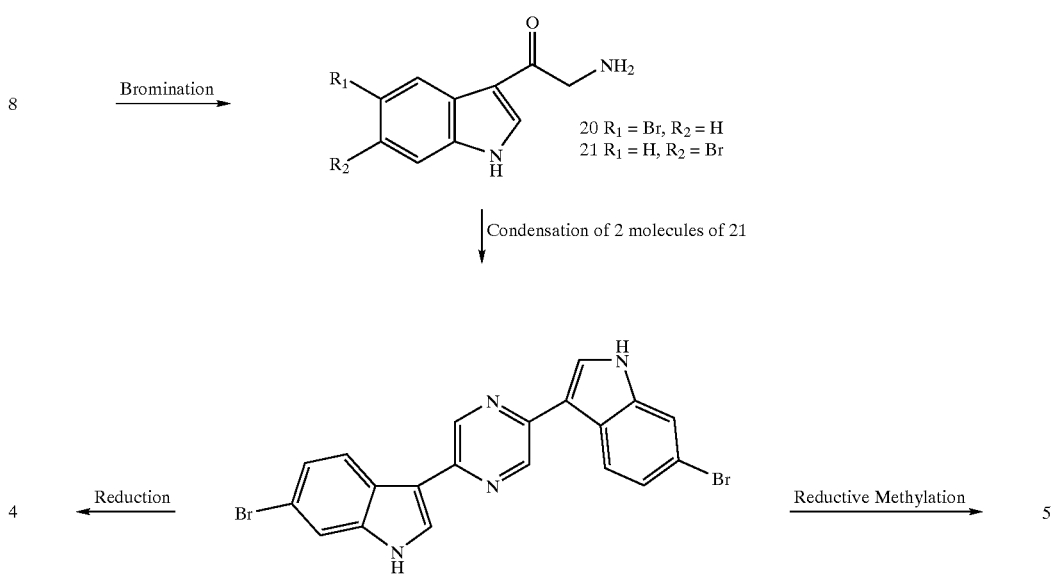

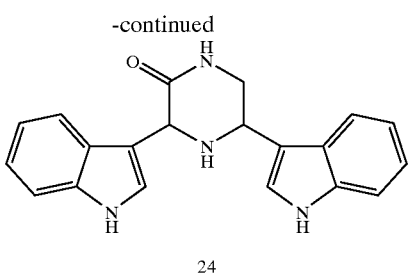

24

Scheme 9 illustrates the synthesis of a different pyrimidinone-linked bisindole compound and its reduction.

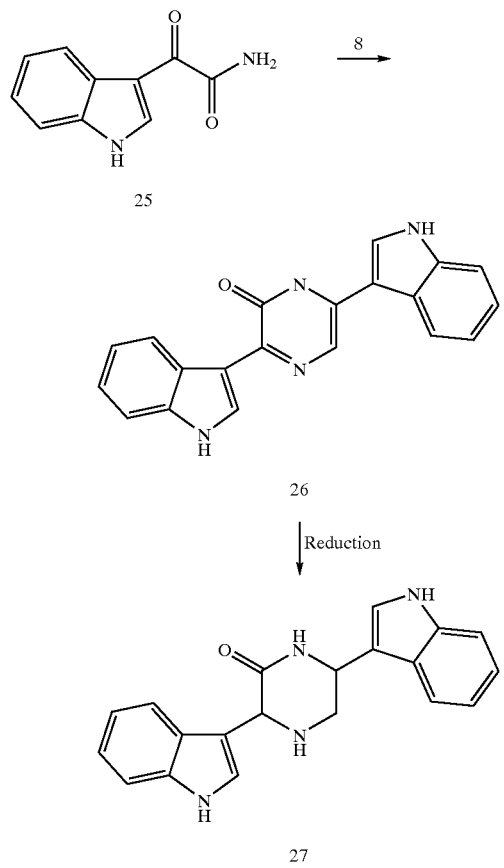

The following examples are provided solely to exemplify certain particular features of working embodiments. Working embodiments are also found in Miyake et al., *Org. Lett.*, 2000, 2, 2121 and Miyake et al., *Org. Lett.*, 2000, 2, 3185 which are incorporated by reference herein. The present invention should not be limited to the particular features described in the examples.

EXAMPLE 1

This example describes the synthesis of acyl cyanide 7 from indole. The synthesis was carried out in two steps according to the method described in Hogan and Sainsbury, *Tetrahedron*, 1984, 40, 681, which is incorporated herein by reference. Briefly, indole is reacted first with oxalyl chloride to provide acid chloride 6. Acid chloride 6 was then reacted with copper (I) cyanide to provide acyl cyanide 7 as a colorless crystalline solid.

EXAMPLE 2

This example describes the synthesis of oxotryptamine 8 from acyl cyanide 7. Four grams of acyl cyanide 7 was exposed to hydrogen in the presence of one gram of 10% Pd/C in acetic acid solution (23° C., 16h) to produce oxotryptamine 8 in 90% yield as the acetate salt.

Spectral data for free base: $^1$H NMR (–300 MHz d$_6$-DMSO), δ8.31 (s, 1H), 8.17 (bd, 1H, J=8), 7.46 (bd, 1H, J=8), 11.7 (bd, 1H), 7.22~7.15 (m, 2H), 3.89 (bs, 2H), 3.35 (br, 2H); $^{13}$C NMR (300 MHz, d$_6$-DMSO), δ 195.3 (s), 136.5 (s), 133.0 (d), 125.4 (s), 122.7 (d), 121.6 (d), 121.2 (d), 114.3 (s), 112.1 (d), 48.2 (t).

Spectral data for HCl salt: $^1$H NMR (300 MHz d$_6$-DMSO), δ 12.45 (bs, 1H, vanishing with D$_2$O), 8.50 (d, 1H, J=2.9Hz), 8.36 (bs, 3H, vanishing with D$_2$O), 8.15 (m, 1H), 7.52 (m, 1H,), 7.23~7.15 (m, 2H), 4.34 (d, 2H, J=5.1, change to s with D$_2$O)

EXAMPLE 3

This example describes the synthesis of amide 9. Acylation of oxotryptamine 8 with acyl cyanide 7 (neat) gave amide 9 in 95% yield.

EXAMPLE 4

This example describes the synthesis of bis(3-indoyl) oxazole 10. Cyclodehydration of amide 9 with phosphorous oxychloride (23° C., 12 hours) produced bis(3-indoyl) oxazole 10 in 90% yield.

EXAMPLE 5

This example describes the synthesis of amide 11. Acylation of oxotryptamine 8 with acid chloride 6 produced amide 11 in 92% yield.

Spectral data: $^1$H NMR (300 MHz, d$_6$-DMSO), δ 12.25 (bs, 1H), 12.05 (bs, 1H), 8.90 (t, 1H, J=5.9), 8.82 (d, 1H, J=2.5), 8.51 (d, 1H, J=2.9), 8.26 (dd, 1H), 8.16 (dd, 1H), 7.54 (dd, 1H) 7.30~7.17 (m, 2H); $^{13}$C NMR (300 MHz, d$_6$-DMSO), δ 189.2, 181.8, 163.7, 138.6, 136.4, 136.8, 133.8, 126.2, 125.4, 128.5, 122.9, 122.6, 121.9, 121.3, 121.1, 113.9, 112.6, 112.3, 112.2, 45.7.

EXAMPLE 6

This example describes the synthesis of oxazole topsentin analog 12. Cylcodehydration of amide 11 with phosphorous oxychloride (23° C., 12 h) afforded the oxazole topsentin analog 12 in 85% yield.

EXAMPLE 7

This example describes the synthesis of nortopsentin D 3. Condensation under neat conditions of commercially available 3-cyanoindole 13 (Aldrich, Milwaukee, Wis.) with oxotryptamine 8 produced nortopsentin D.

Spectral data: Free Base $^1$H NMR (300 MHz, d$_6$-Acetone), δ 10.56 (s, 1H), 10.38 (s, 1H) 8.57 (dd, 1H, J=8.4), 8.05 (dd, 1H, J=8.4), 8.00 (d, 1H, J=2.0), 7.83 (s, 1H), 7.47~7.45 (m, 2H), 7.45 (s, 1H), 7.21~7.10 (m, 4H); Free Base $^1$H NMR (300 MHz, d$_6$-DMSO), δ 12.30 (s, 1H), 11.37 (s, 1H), 11.18 (s, 1H), 8.41 (bd, 1H, J=7.1), 7.99 (bd, 1H, J=7.4), 7.93 (d, 1H, J=7.4), 7.74 (d, 1H, J=2.1), 7.41 (s, 1H), 7.45~7.43 (m, 2H), 7.19~7.07 (m, 4H); HCl salt $^1$H NMR (300 MHz, d$_6$-DMSO), δ 14.54 (bs, 1H), 14.15 (bs, 1H), 12.32 (bs, 1H,), 11.73 (bs, 1H) 8.63 (d, 1H, J=2.9), 8.38 (d, 1H, J=2.6), 8.14 (bd, 1H, J=6.9), 7.95 (bd, 1H, J=6.9), 7.95 (s, 1H, 1H, J=6.9), 7.51 (bd, 1H, J=7.8) 7.33~7.15 (m, 4H); HCl salt $^{13}$C NMR (300 MHz, d$_6$-DMSO), δ 140.1 (s), 136.4 (s), 136.3 (s), 130.0 ,127.9, 125.5, 124.01, 123.3, 123.0, 122.2, 121.1, 120.2, 119.5, 119.3, 112.6, 112.2 (d), 112.1 (d), 102.5, 99.0.

EXAMPLE 8

This example describes the synthesis of 6-bromocyanoindole 14. Direct bromination of 3-cyanoindole 13 with NBS over silica in CH$_2$Cl$_2$ (Mistry et al, *Tetrahedron Lett.*, 1986, 27, 1051, incorporated herein by reference) gave a 50% yield of bromoindole 14 as the major product. Small amounts (10%) of the 5-substituted regioisomer were also observed. Although the yield was modest, the preparation of 14 requires only one step from commercially available 3-cyanoindole and is easily separated from the minor regioisomer by flash chromatography. HMQC correlations confirmed the position of substitution.

EXAMPLE 9

This example describes the synthesis of nortopsentin B 2. Condensation of oxotryptamine 8 with nitrile 14 under neat conditions produced nortopsentin B 2. All spectral data for synthetic nortopsentin B were identical to those reported for the natural material reported by Sakemi and Sun, *J. Org. Chem.*, 1991, 56, 4304.

EXAMPLE 10

This example describes the preparation of topsentin A 1. Oxidative dimerization of oxotryptamine 8 in NH$_4$OH and air at 100° C. gave topsentin A 1 in 80% yield. All spectral data for synthetic topsentin A 1 were identical to those reported for the natural material reported by Bartik et al., *Can. J. Chem.*, 1987, 65, 2118.

Spectral data: Free base $^1$H NMR (300 MHz, d$_6$-Acetone), δ 12.12 (bs, 1H), 12.04 (bs, 1H) 11.14 (bs, 1H), 11.09 (bs, 1H), 10.38 (bs, 9.64 (d, J=3), 9.41 (d, J=3.0), 8.55~8.5 (m), 8.23 (bd), 8.09 (d), 7.97 (bd), 7.85 (d, J=2.4), 7.72 (d, J=2.1) 7.63 (d), 7.61~7.47 (m), 7.29~7.11 (m); Free base $^1$H NMR (300 MHz, d$_6$-DMSO), δ 13.21 (bs,_), 13.12 (bs) 12.10 (bs), 12.04 (bs), 11.44 (bs), 11.22 (bs), 9.39 (d, J=3.0), 9.18 (d, J=3.1), 8.42~8.39 (m), 8.16 (d, J=7.4), 8.10 (d, J=2.4), 7.90 (d, J=7.4), 7.83 (d, J=2.3) 7.68 (d, J=2.1), 7.62 (d, J=0.9) 7.56~7.51 (m ), 7.44 (bt, J=7.0) 7.27~7.22 (m) 7.18~7.08 (m); $^{13}$C NMR (300 MHz, d$_6$-Acetone), δ 177.14, 177.06, 146.6 (s), 140.2 (s), 138.0 (d), 137.9 (s), 137.8 (s), 137.6 (d), 137.4 (s), 137.35 (s), 131.0, 128.08 (d), 127.11 (d), 126.5 (s), 126.0 (s), 124.25, 123.87, 123.79, 123.21, 123.00, 122.79, 122.70, 122.41, 121.26, 121.03, 120.47, 120.33, 115.41, 115.03, 112.76, 112.34, 111.93, 106.58; HCl salt $^1$H NMR (300 MHz, d$_6$-DMSO), δ 12.56 (bs, 1H), 11.67 (bs, 1H), 8.87 (bs, 1H), 8.32~8.29 (m, 1H), 8.13 (d, 1H, J=8.13), 8.01 (s, 1H), 8.00 (d, 1H), 7.60~7.57 (m, 1H) 7.49 (d, 1H, J=7.5), 7.33~7.27 (m, 2H), 7.23~7.13 (m, 4H); $^{13}$C NMR (300 MHz, d$_6$-DMSO), δ 172.4 (s), 141.5 (s), 138.5 (d), 136.7 (s), 136.4 (s), 131.6 (s), 126.0 (s), 125.4 (d), 124.2 (s), 123.8 (d), 122.7 (d), 122.1 (d), 121.3 (d), 120.2 (d), 119.5 (d), 116.7 (d), 113.4 (s), 112.7 (d), 112.2 (d), 103.3 (s).

EXAMPLE 11

This example describes the preparation of amino alcohol 15. Acyl cyanide 7 was reduced with lithium aluminum hydride (LiAlH$_4$) according to the method disclosed by Burger and Hombaker, *J. Am. Chem. Soc.*, 1952, 74, 5514 (incorporated herein by reference) to provide amino alcohol 15 in 60% yield.

Spectral data: $^1$H NMR (300 MHz d$_6$DMSO), δ 11.01 (bs, 1H), 7.66 (d, 1H, J=7.8), 7.39 (d, 1H, J=8.1), 7.24 (s, 1H), 7.09 (t, d, 1H, J=7.5, 1.1), 6.99 (td, 1H, J=7.4, 1.0), 4.82 (dd, 1H, J=6.8, 5.2), 3.25 (b, 3H), 2.92 (dd, 1H, J=12.7, 5.2), 2.87 (dd, J=12.7, 6.8); $^{13}$C NMR (300 MHz, d$_6$-DMSO), δ137.3 (s), 126.8 (s), 123.03 (d), 121.78 (d), 120.18 (d), 119.16 (d), 118.42 (s), 112.32 (d), 69.73 (d), 49.64 (t).

EXAMPLE 12

This example describes the preparation of symmetrical dimer 17. Heating 15 in 4:1 xylene/EtOH solution at 130° C. under a sealed atmosphere of argon followed by exposure to air and filtration gave dimer 17 (30%) and indole (20%) as the major products.

EXAMPLE 13

This example describes the preparation of pyrazine 16. Heating oxotryptamine 8 in a 4:1 xylene/EtOH solution at 130° C. for 3 days under a sealed atmosphere of argon followed by exposure to air and filtration gave pyrazine 16 in 85% yield.

Spectral data: C$_{20}$ H$_{14}$ N$_4$, Fab (C$_{20}$H$_{15}$N$_4$) Mass 311.13001, Calculated. 311.12967; $^1$H NMR (300 MHz) (in d$_6$ DMSO), δ 11.62 (bs, 2H), 9.12 (s, 2H), 8.43 (d, 2H, J=7.2), 8.22 (d, 2H, J=2.6), 7.47 (d, 2H, J=7.6), 7.21~7.11 (m, 4H); $^{13}$C NMR (300MHz) d$_6$-DMSO, δ 146.7 (size), 140.1 (d, 2C), 137.0 (s, 2C), 125.6 (d, 2C), 125.2 (s, 2C), 122.0 (d, 2C), 121.5 (d, 2C), 120.1 (d, 2C), 112.7 (s, 2C), 111.9 (d, 2C).

EXAMPLE 14

This example describes the preparation of piperazine 18. Pyrazine 16 was reduced to piperazine 18 in 70% yield with NaBH$_3$CN in acetic acid using the reaction conditions described by Gribble et al., *J. Am. Chem. Soc.*, 1974, 96, 7812 (incorporated herein by reference). Only the thermodynamically more stable trans diequatorial isomer was detected.

Spectral data: $^1$H NMR (300 MHz, d$_6$-DMSO), δ 10.85 (bs, 2H), 7.70 (d, 2H, J=7.73), 7.34 (d, 2H, J=7.96), 7.25 (d, 2H, J=2.1), 7.05 (t, 2H, J=7.00), 6.97 (t, 2H, J=6.94), 4.07 (dd, 2H, J=10.1, 2.3), 3.18 (dd, 2H, J=11.5, 2.3), 2.87 (dd, 2H, J=11.5, 10.1), 2.58 (br, 2H); $^{13}$C NMR (300 MHz, d$_6$-DMSO), 6 137.1 (s, 2C), 127.0 (s, 2C), 122.6 (2C), 121.7 (2C), 120.1 (2C), 119.0 (2C), 117.8 (2C), 112.3 (2C), 55.0 (2C), 54.2 (2C).

EXAMPLE 15

This example describes the preparation of dimethyl piperazine 19. Pyrazine 16 was treated with NaBH$_3$CN in formic acid under conditions similar to those used in Example 14. Pyrazine 16 underwent reductive methylation to provide dimethyl piperazine 19 in 60% yield.

EXAMPLE 16

This example describes the synthesis of halogenated oxotryptamines 20 and 21. Oxotryptamine 8 was brominated with NBS over silica in CH$_2$Cl$_2$ (Mistry et al, *Tetrahedron Lett.*, 1986, 27, 1051, incorporated herein by reference) to give an isomeric mixture of 5- and 6-substituted indole derivatives 20 and 21 in an approximate 2:1 ratio, respectively. The isomers were separated by flash chromatography.

EXAMPLE 17

This example describes the synthesis of pyrazine 22. Condensation of halogenated oxotryptamine 22 by heating (130° C.) in 4:1 xylene/EtOH under a sealed atmosphere of argon for 3 days followed by exposure to air and filtration gave pyrazine 22 in 75% yield.

EXAMPLE 18

This example describes the synthesis of dragmacidin B 4. Selective reduction of the pyrazine ring using NaBH$_3$CN in formic acid (See, Example 14 for conditions) gave dragmacidin B 4 in 70% yield. Spectral data were consistent with those reported for natural dragmacidin B.

EXAMPLE 19

This example describes the synthesis of 2,5-bis(6'-bromo-3'-indoyl) piperazine 5. Reductive methylation using NaBH$_3$CN in acetic acid (See, Example 14 for conditions) gave piperazine 5 in 60% yield.

EXAMPLE 20

This example describes the synthesis of compound 23. Compound 9 (0.05g) was heated in NH$_4$OH at 100° C. for 30 hours under nitrogen to provide 23 in 70% yield.

Spectral data: $^1$H NMR (300 MHz, d$_6$-DMSO), δ 12.24 (bs, 1H), 11.60 (bs, 1H), 11.32 (bs, 1H), 8.87 (d, 1H, J=2.8), 8.77 (d, 1H, J=7.6), 8.02 (d, 1H, J=7.7), 7.83 (d, 1H, J=2.5), 7.48 (s, 1H), 7.50~7.46 (m, 2H), 7.23~7.06 (m, 4H); $^{13}$C NMR (400 MHz, d$_6$-DMSO), δ 154.6 (s), 151.2 (s), 137.7 (s), 137.1 (s), 132.2 (d), 130.9 (s), 126.9 (s), 125.4 (s), 124.1 (d), 123.5 (d), 123.0 (d), 122.3 (d), 121.3 (d), 120.8 (d), 120.2 (d), 117.2 (s), 114.2 (s), 112.9 (d), 112.8 (d), 112.6 (d).

EXAMPLE 21

This example describes the synthesis of compound 24. Compound 23 (0.016 g) was treated with 0.125 g NaBH$_3$CN in 15 mL of acetic acid to provide 24.

EXAMPLE 22

This example describes the synthesis of compound 26. Compound 25 (0.3 g) was reacted neat with compound 8 (0.2 g) at 220° C. for 4 hours to provide 26 in 60% yield.

Spectral data: $^1$H NMR (300 MHz, d$_6$-DMSO) δ 12.21 (br, 1H), 1173 (br, 1H), 11.50 (br, 1H), 8.74 (bs, 1H), 8.68 (d, 1H, J=7.8), 8.10 (d, 1H, J=2.2), 7.25 (br, 2H), 7.50–7.45 (m, 2H), 2.25–7.11 (4H); $^{13}$C NMR (400 MHz, d$_6$-DMSO) δ 156.4, 146.7, 137.7, 137.1, 130.9, 127.1, 126.8, 124.9, 123.6, 123.1, 122.9, 121.4, 121.0, 120.7 (d), 113.1, 112.8, 112.5, 107.7.

EXAMPLE 23

This example describes the synthesis of compound 27. Compound 26 is treated with NaBH$_3$CN in acetic acid to provide 27.

The present invention has been described with respect to certain embodiments. The scope of the invention should not be limited to these described embodiments, but rather should be determined by reference to the following claims.

We claim:

1. A method for converting an acyl cyanide to an alpha amino ketone, comprising:

providing a first acyl cyanide having the formula

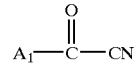

wherein A$_1$ has the formula

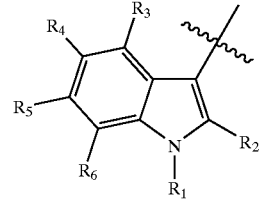

where R$_1$, R$_2$, R$_3$, R$_4$, R$_5$, and R$_6$ are independently selected from the group consisting of hydrogen, hydroxy, halogen, lower aliphatic, lower alkoxy, and lower acyl; and hydrogenating the first acyl cyanide to convert the first acyl cyanide to first alpha amino ketone.

2. The method of claim 1, wherein hydrogenating the first acyl cyanide to convert the first acyl cyanide to the first alpha amino ketone comprises exposing the first acyl cyanide to hydrogen in the presence of a hydrogenation catalyst.

3. The method of claim 2, wherein the hydrogenation catalyst is palladium carbon.

4. The method of claim 1, wherein R$_{1-6}$ are hydrogen.

5. The method of claim 1, wherein at least one of R$_{1-6}$ is halogen.

6. The method of claim 5, wherein R$_4$ or R$_5$ is bromine.

* * * * *